(12) United States Patent
Kashefi-Khorasani et al.

(10) Patent No.: US 8,398,858 B2
(45) Date of Patent: Mar. 19, 2013

(54) DEVICE FOR TRANSFERRING MASS AND/OR EXCHANGING ENERGY

(75) Inventors: Ahmad Ali Kashefi-Khorasani, Aachen (DE); Bernward Oedekoven, Bocholtz (NL); Rainer Dautzenberg, Aachen (DE)

(73) Assignee: Dritte Patentportfolio Beteiligungsgesellschaft mbH & Co. KG, Schonefeld/Waltersdorf (DE)

( * ) Notice: Subject to any disclaimer, the term of this patent is extended or adjusted under 35 U.S.C. 154(b) by 503 days.

(21) Appl. No.: 12/529,095

(22) PCT Filed: Feb. 26, 2008

(86) PCT No.: PCT/EP2008/001487
§ 371 (c)(1),
(2), (4) Date: Aug. 28, 2009

(87) PCT Pub. No.: WO2008/104353
PCT Pub. Date: Sep. 4, 2008

(65) Prior Publication Data
US 2010/0106072 A1 Apr. 29, 2010

(30) Foreign Application Priority Data
Feb. 28, 2007 (DE) .......................... 10 2007 010 112

(51) Int. Cl.
  *B01D 11/00* (2006.01)
  *B01D 61/00* (2006.01)
  *C02F 1/44* (2006.01)

(52) U.S. Cl. ...................................... 210/645; 604/6.14

(58) Field of Classification Search .................. 604/4.01, 604/5.01, 6.13, 6.14, 6.16; 210/645, 646
See application file for complete search history.

(56) References Cited

U.S. PATENT DOCUMENTS

| 4,490,331 A | 12/1984 | Steg, Jr. |
| 5,110,548 A | 5/1992 | Montevecchi et al. |
| 5,116,308 A | 5/1992 | Hagiwara |

FOREIGN PATENT DOCUMENTS

| EP | 0 378 225 A2 | 7/1990 |
| EP | 0 534 386 A2 | 3/1993 |
| EP | 534386 A2 * | 3/1993 |
| JP | 50-009299 A | 1/1975 |

(Continued)

OTHER PUBLICATIONS

Machine English translation of specification, EP 534,386 A2 to Oedekoven et al.*
Letter to EP Patent Office dated Jun. 1, 2009 in counterpart EP Application No. 08716030.5.

(Continued)

*Primary Examiner* — Melanie Hand
(74) *Attorney, Agent, or Firm* — Panitch Schwarze Belisario & Nadel LLP (57) ABSTRACT

A device is provided for transferring mass and/or exchanging energy between two media, particularly between blood and a gas/gas mixture. The device includes a chamber (2), through which the first medium flows and inside which at least one mass-permeable and/or energy-permeable hollow fiber (5), preferably a plurality of mass-permeable and/or energy-permeable hollow fibers (5), is/ are arranged. The second medium can flow through the at least one hollow fiber (5), while the first medium can flow therearound. At least one pumping element (5), which allows the first medium to be displaced from the chamber (2) and/or to be sucked into the chamber (2), is disposed in the chamber (2) of the device.

21 Claims, 5 Drawing Sheets

FOREIGN PATENT DOCUMENTS

| | | | |
|---|---|---|---|
| JP | 02161953 | A | 6/1990 |
| JP | 3047268 | A | 2/1991 |
| JP | 06296687 | A | 10/1994 |
| JP | 2001070442 | A | 3/2001 |
| WO | 99/04832 | A1 | 2/1999 |

OTHER PUBLICATIONS

Office Action issued May 25, 2012 in Japanese Patent Application No. 2009-551121.

* cited by examiner

DEVICE FOR TRANSFERRING MASS AND/OR EXCHANGING ENERGY

CROSS-REFERENCE TO RELATED APPLICATIONS

This application is a Section 371 of International Application No. PCT/EP2008/001487, filed Feb. 26, 2008, which was published in the German language on Sep. 4, 2008, under International Publication No. WO 2008/104353 A1 and the disclosure of which is incorporated herein by reference.

BACKGROUND OF THE INVENTION

The invention relates to a device for the mass transfer and/or energy exchange between two media, particularly between blood and a gas/gas mixture, the device comprising a chamber through which the first medium flows and in which at least one mass and/or energy-permeable hollow fiber is disposed, preferably a plurality of mass and/or energy-permeable hollow fibers are disposed, through which a second medium can flow and around which the first medium can flow.

Generic devices of this type are used, for example, in medical technology, and there in particular in applications for blood purification, such as dialysis, blood separation or also artificial lungs (oxygenators).

In the field of application of oxygenators, it is provided to this end that the blood as a first medium is allowed to flow through a chamber, in which at least one mass and/or energy-permeable hollow fiber is disposed, or in a preferred embodiment a plurality of mass and/or energy-permeable hollow fibers are disposed, through which the second medium, in this case particularly oxygen, can flow and around which the first medium flows.

If in this version blood originating from the body of a living being and aerated with $CO_2$ is pumped through the chamber, the different partial pressures of oxygen and $CO_2$ on the two sides of the mass and/or energy-permeable hollow fiber produce a mass transfer in the sense that $CO_2$ is removed from the blood and the same is oxygenated with oxygen from the hollow fibers. In this way, such a device can operate as an artificial lung and assume, for example, the lung function of a patient, either partially or also completely.

Insofar as an oxygenator, i.e., an artificial lung, is described in more detail in this specification, it shall not be interpreted as a restriction, but only as an application by way of example. The device according to the invention described below can in principle be used for the mass transfer and/or energy exchange between arbitrary media, and not only in medical technology, but also in other industrial applications.

In order to achieve adequate and defined flow rates of a first medium through the afore-mentioned chamber, in particular of the blood through the chamber, external pumps are required. In the range of applications of the oxygenators, this means that in addition to the generic device an external pump must be provided, which is used to ensure that blood is pumped from the body of a patient through the device and then back into the body of the patient. In this respect, the body of a patient shall denote both the body of a human and that of an animal patient.

When looking overall at the generic devices and the externally employed pumps, this principle mentioned above causes a significant volume which must be filled by the first medium, in this application the blood, for example.

Particularly with babies, and specifically premature babies, who have a very low blood volume, at times less than 100 milliliters, this means that the generic known devices cannot be employed, or great stress is caused to the organism of a baby by the addition of donor blood, blood plasma, or plasma expander, in order to be able to fill the volumes of the known devices. Furthermore, the use of such generic known devices is also possible only outside the body of a patient due to the additional pumps.

BRIEF SUMMARY OF THE INVENTION

It is the object of the invention to refine a generic known device such that a compact version is achieved, particularly one that requires a minimal filling volume and moreover also opens up the use as an implantable device.

This object is achieved by a device of the generic type mentioned above, a pump function being provided in the afore-mentioned chamber.

For this purpose, for example, a pump element can be integrated in the device, particularly in the chamber, for example by at least one deformable, particularly elastically deformable element, the surface/volume of which can be varied at least in some regions, such that in the case of a surface/volume increase the first medium can be displaced from the chamber, and in the case of a surface/volume reduction the first medium can be suctioned into the chamber.

The essential core idea of this aspect according to the invention is that with this version a pump function can be integrated directly in the device, thereby eliminating an extracorporeal additional pump. The pump effect is achieved in that due to the increase in the surface of a deformable, particularly elastically deformable element, and the associated volume increase, the first medium present in the afore-mentioned chamber, such as blood, is automatically displaced, and with a subsequent surface or volume decrease of this element, the first medium, for example blood, is again suctioned into the chamber due to the resulting negative pressure.

To this end, it must be ensured that the process of displacement always causes the first medium treated as desired by the mass transfer and/or energy exchange to be displaced, and during suctioning the untreated medium to be suctioned.

This can be achieved in that a flow direction through the chamber is defined, which in a preferred embodiment of the invention can take place in that, in the flow path at least one one-way valve is disposed, and preferably that a one-way valve is disposed in the chamber at each of the inlet and the outlet for the first medium.

The first medium can flow through such a valve only in one direction, so that in a version having two valves the suctioning of the first medium can always take place through the one valve and the displacement of the first medium can always take place through the other valve. The arrangement of these valves directly in the chamber, or at the inlet or outlet of the chamber, thus results further in a reduction of the size and in a preferred compactness of the device according to the invention, since such means for defining the flow direction in this case no longer have to be provided externally.

The deformable element can be controlled, for example, from outside the device, for which different measures are available. For example, it may be provided that the deformable element solely changes the shape thereof, and consequently the surface size or the volume thereof, in that it is controlled electrically or electronically and/or hydraulically and/or pneumatically.

For example, the deformable element may be configured as a balloon and thereby form an inflatable and deflatable envelope, which additionally can also be designed to be elastic. In this way, the pump effect can be achieved, for example, through periodic filling and emptying by a fluid (gas or liquid).

In a particularly preferred embodiment, it may also be provided that the at least one deformable element is configured as a deformable, particularly elastically deformable hollow fiber, the surface/volume of which can be varied at least in regions by inner pressurization with a medium. For example, if such a particularly elastic hollow fiber is filled by a fluid medium, such as a gas or even a liquid, then by varying the pressure of this medium it can be achieved that the surface, and consequently the volume taken up by the hollow fiber in the chamber, is increased. In this way too, the desired pump effect according to the invention can be achieved. Furthermore, by generating a negative pressure inside the hollow fiber, the volume in the chamber can be increased. In this way, by subjecting the hollow fiber to pressure, an increased "stroke volume" can be achieved.

According to one embodiment of the invention, it may be provided that in the device mass and/or energy-permeable hollow fibers are provided, particularly at least one that is used only for the mass transfer and/or energy exchange, and that at least one elastically deformable hollow fiber is used, which is integrated in the device for the pump purposes. To this end, one or more of the hollow fibers used for mass transfer or energy exchange can be used, and this also applies to the hollow fiber used for the pump purposes. The mass and/or energy-permeable hollow fibers can also be rigid hollow fibers.

In another preferred embodiment, it may also be provided that the at least one elastically deformable hollow fiber is configured as a mass and/or energy-permeable hollow fiber. For example, for this purpose an elastically deformable and mass and/or energy-permeable hollow fiber can be configured as a silicone hose, since silicone, particularly in the application as an oxygenator, is permeable to oxygen and carbon monoxide, such that not only the gas exchange between the gas phase and the blood phase of a device according to the invention can be carried out through a silicone hose, but also that the pump function can be implemented due to the elastic deformation property.

In a particularly simple and accordingly compact and cost-effective embodiment, it can thus be provided that a device has only a single, particularly elastically deformable and simultaneously mass and/or energy-permeable hollow fiber, which both assumes the pump function of the first medium, and transports the second medium, by which a mass transfer and/or energy exchange is to take place. Of course, instead of a particularly elastically deformable and mass and/or energy-permeable hollow fiber, it is also possible to use an arbitrary number of energy-permeable deformable hollow fibers. The device may then comprise only hollow fibers of the elastic and permeable type. In this embodiment, it may therefore be provided that the medium for pressurization of the at least one elastically deformable hollow fiber corresponds to the second medium.

In another embodiment, it may also be provided that at least some of all mass and/or energy-permeable hollow fibers are also configured as elastically deformable hollow fibers. In such an embodiment, for example, there may be mass and/or energy-permeable hollow fibers, which are configured as rigid hollow fibers, as well as mass and/or energy-permeable hollow fibers, which are elastically deformable, as mentioned above. To this end, one or more of each type of the hollow fibers may be provided.

In yet another embodiment, the elastically deformable hollow fibers can be used solely for pump purposes, particularly without them being mass-permeable, but optionally being energy-permeable.

Accordingly, particularly in the last embodiments having two different types of hollow fibers (pump fibers and mass transfer fibers), it may be provided that the medium for pressurization of the at least one elastically deformable hollow fiber, i.e., the medium used for implementing the pump function, does not correspond to the second medium, but is formed by yet another fluid medium, such as a gas or a liquid. To this end, it may additionally be provided that through the use of this medium also a heat exchange with the first medium is implemented.

This is particularly advantageous, for example, in the use for blood oxygenators, since here, in addition to the pump effect, which is implemented by the other or additional medium, it can also be ensured that sufficient thermal energy is transmitted to the first medium, in this application it being the blood, in order to maintain the body temperature of the patient. Since the first medium, in this application it being the blood, flows around the hollow fiber at least in the region of the elastic hollow fiber in which a surface or volume increase takes place, accordingly at the same time a thermal energy transfer to the first medium can take place.

The generation of a pump function inside the chamber of the device, through which the first medium flows, which is to say blood, for example, in addition to the pure pump effect also has the added advantage that a disturbance is caused by the pressure fluctuations in the chamber, whereby a plasma edge, which may form on the chamber side on the mass-permeable hollow fibers, can be destroyed or at least disturbed, in order to optimize the efficiency of the mass and/or energy transfer.

In a further preferred embodiment according to the invention, it may also be provided that, in addition to the above-mentioned chamber, through which the first medium flows, at least one other chamber is provided, by which the second medium is fed to the at least one mass and/or energy-permeable hollow fiber, preferably to the plurality of mass and/or energy-permeable hollow fibers, wherein the at least one elastically deformable hollow fiber extends through the above-mentioned and the at least one further chamber.

This produces the advantage that, due to the extension of the deformable fiber also through the other chamber, a heat exchange, particularly a heat transfer to the second medium, can optionally also take place, such that a heat transfer after heating of the second medium can also take place by way of the mass-permeable hollow fibers to the first medium.

Furthermore, the embodiment may be such that the surface/the volume of the at least one particularly elastically deformable hollow fiber can also be varied at least in some regions in the at least one other chamber by inner pressurization with the medium, such that in the case of a surface/volume change, pressure fluctuations can be generated in the second medium. These pressure fluctuations can advantageously cause a gas boundary layer, which forms by the phase of the second medium or by the gas phase on the mass-permeable hollow fiber, to be disturbed or destroyed, thereby improving or optimizing the mass transfer and/or energy exchange.

In all embodiments mentioned above, be it with only one or also several chambers, it may be provided that the surface/volume change of the at least one particularly elastically deformable hollow fiber can be generated by pressure changes of the medium flowing through this hollow fiber.

To this end, as mentioned above, it can be a fluid medium, such as a gas or also a liquid. The pressure changes can be generated by a continuous inflow of this medium into the at least one particularly elastically deformable hollow fiber at the inlet into the device, and an outflow, the quantity of which can be controlled, at the outlet of the device, particularly by a cross-section that can be varied in a controlled manner.

For example, the controllably variable cross-section at the outflow can be reduced in a targeted manner, or even be closed, whereby with a continuous inflow on the inlet side the pressure in the particularly elastically deformable hollow fiber is increased, wherein due to the elastic deformation, the volume taken into the chamber is increased and the first medium, in this case particularly blood, is displaced. If the controllably variable cross-section is increased, particularly after prior closure, the pressure is reduced, for example by an elastically restoring force, and the volume of the hollow fiber can be reduced, such that the originally displaced volume of the first medium is compensated for by the subsequent suctioning of first medium into the chamber.

In all embodiments, it may be provided that a particularly elastically deformable hollow fiber can be deformed across the entire length thereof, which it takes up in the at least one chamber of the device. In another embodiment, it may also be provided that the variation of the surface size or of the volume is intentionally limited to only certain regions, particularly at least one region of the elastically deformable hollow fiber. For example, in order to generate at least one locally delimited region of this surface or volume change, a deformable, particularly elastic, hollow fiber can have at least one supporting element at least partially surrounding the same. Such a supporting element can be, for example, a ring, a tube, or also a lattice, which surrounds the elastic hollow fiber at least partially, such that in the surrounded region no volume or surface increase can take place, but only in the regions that remain free of the supporting element.

In another embodiment, it may also be provided that for the generation of at least one locally delimited region of the surface or volume variation an elastic hollow fiber has a regionally variable wall thickness and/or a surface profile. If, for example, the wall thickness is reduced in a certain region compared to other regions, then the elastic hollow fiber will tend to significantly bulge in this thickness-reduced region due to the pressure increase acting from inside the fiber.

With all these above-mentioned measures, the displacement volume of an elastic hollow fiber can therefore be precisely defined.

In addition, it may also be provided that a particularly elastically deformable hollow fiber is disposed, for example, in a cage, which limits the maximum displaced volume. For example, during an inflation of a hollow fiber, the fiber can expand only so much and increase the volume thereof until the wall regions of the elastic hollow fiber rest against the inside regions of the surrounding cage. The hollow fiber is then supported by the cage and cannot expand any further, so that the effectively displaced volume is determined by the maximum volume of the surrounding cage.

It is also possible that a hollow fiber comprises a section that cannot be elastically deformed and that cannot be elastically inflated by inner pressurization, such as in the manner of a plastic bag, until the maximum volume of this region has been reached. Upon a decrease in pressure, this region can again actively collapse, particularly be folded, by restoring forces, particularly spring forces. To this end, for example, spring elements (at least one) can be disposed in the wall of the deformable section.

The arrangement of the at least one particularly elastically deformable hollow fiber and the mass and/or energy-permeable hollow fibers, which optionally according to one embodiment can also be identical to each other, can in principle be arbitrary.

According to the invention, however, it is found to be particularly advantageous if at least one elastically deformable hollow fiber is surrounded by a plurality of non-elastic and mass and/or energy-permeable hollow fibers, particularly in a symmetrical manner. Again, the surrounded deformable hollow fiber can likewise be configured to be mass and/or energy-permeable, or optionally may only be provided for the pump function. This arrangement can preferably be configured such that the overall arrangement of hollow fibers has a substantially polygonal, particularly hexagonal cross-section.

In order to achieve a particularly high packing density, it may be provided that the non-elastic and mass and/or energy-permeable hollow fibers are disposed offset from each other, particularly layered offset by half a distance between two hollow fibers. In such an embodiment, for example, the mass and/or energy-permeable hollow fibers can be configured as mats, which are layered on top of each other, in this case particularly offset by half the distance, such that a hollow fiber of a second mat, which is placed on a first mat, ends up exactly between two hollow fibers of the first mat. In this way, the high packing density mentioned above is achieved.

The device according to the invention has the particular advantage that high efficiency is achieved, particularly also due to the claimed and above-described disturbance of the plasma edges or gas boundary layers on both sides of the mass-permeable hollow fibers, wherein due to the high efficiency and the integrated pump function, a very compact shape can be achieved, particularly implemented with the fill volumes of the first medium in the device of less than 100 ml.

In a particularly preferred manner, such devices can thus be employed, for example, as blood oxygenators, particularly for babies and/or premature babies, and can also be used as implantable oxygenators, for example if the function of a lung lobe has to be supported or even entirely replaced.

In addition, it also lends itself to use the device according to the invention as an arbitrary implantable artificial organ, for example also as a dialysis unit (artificial kidney) or also as an artificial liver. In this respect, it is only required to define for what type of mass transfer the device is supposed to be suited, based on the first and second, and optionally also third, media that are employed and the mass and/or energy-permeable hollow fibers that are employed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Below, the prior art and the embodiments according to the invention are described by way of a blood oxygenator in order to highlight the key advantages according to the invention. This example shall not be understood to be limiting and shall be applied analogously also to the mass transfer and/or energy exchange between other media.

Figure 1A:
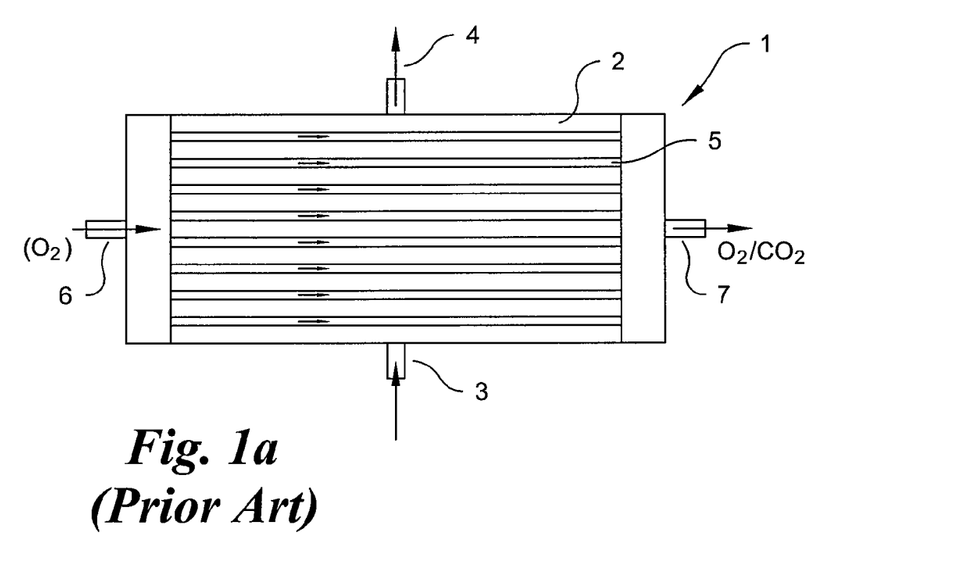
FIGS. 1a and 1b are schematic views showing the fundamental design of a blood oxygenator known from the prior art.
Figure 1B:
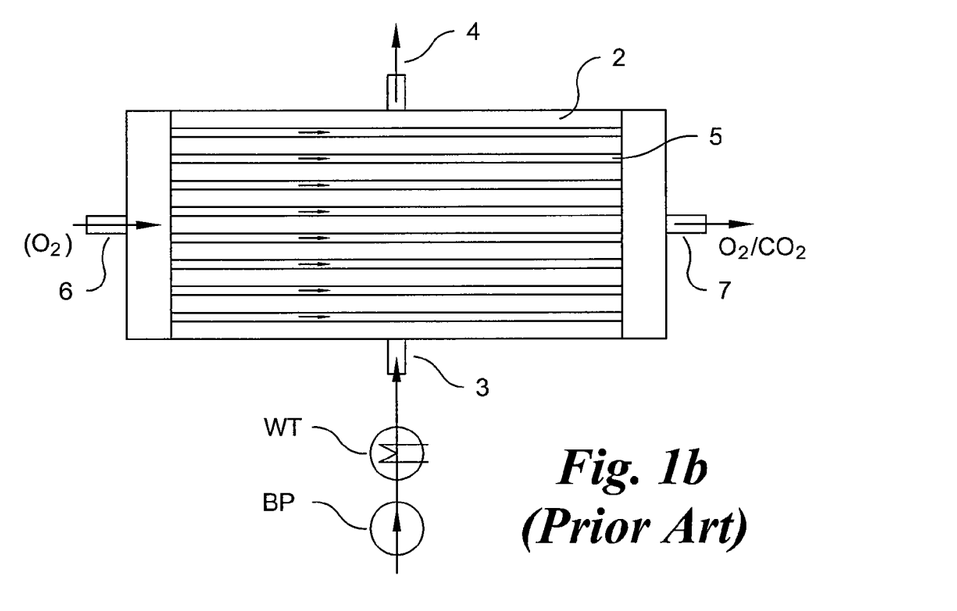

FIGS. 1a and 1b show the known schematic design of a blood oxygenator, comprising a device 1 having a chamber 2, which has a blood inlet 3 and a blood outlet 4. Accordingly, blood can flow through this chamber via the blood inlet and blood outlet, here substantially transversely to the longitudinal extension of the device 1.

In the direction of the longitudinal extension, a plurality of mass-permeable, in this example particularly oxygen and carbon dioxide-permeable, hollow fibers 5 extend through the chamber 2 in the axial direction, such that oxygen can be added to the device through the gas inlet 6 on the left, the oxygen exiting the device through the gas outlet 7 on the right. If accordingly used blood, i.e., blood aerated with $CO_2$, is pumped into the chamber 2 by an external pump, which is not shown here, then due to the high partial pressure difference on both sides of the hollow fibers 5 a gas exchange takes place, during which $CO_2$ is transferred out of the blood into the gas phase and oxygen is transferred from the gas phase into the blood. With a continuous pump function, in this way, used blood from the body of a patient can be oxygenated and pumped back into the body of the patient.

The embodiment of a known classic blood oxygenator shown here has the disadvantages of a large shape and the necessity of an external pump.

Figure 2:
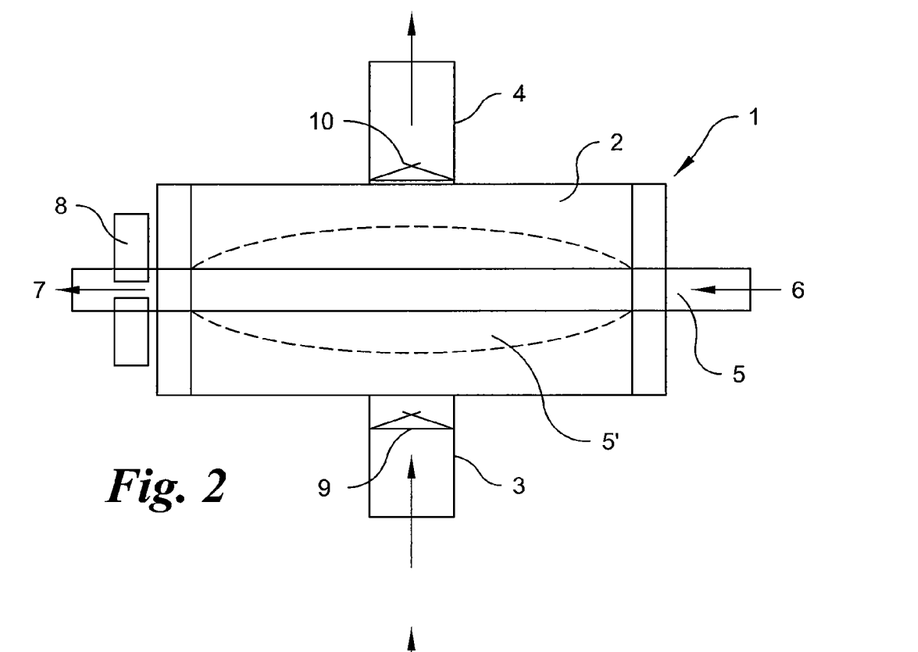
FIG. 2 is a schematic view showing the fundamental design of a blood oxygenator according to an embodiment of the present invention, comprising only one mass-permeable hollow fiber, which at the same time serves as a pump, due to the elastic deformability thereof.

FIG. 2 shows a simple embodiment of a blood oxygenator designed according to the invention, which again is configured as a device 1 having an inner chamber 2 comprising a blood inlet 3 and a blood outlet 4. An elastically deformable and at the same time mass and/or energy-permeable hollow fiber 5 extends through the chamber 2 transversely to the flow direction of the blood, wherein oxygen flows through the hollow fiber 5, in this example in the application of a blood oxygenator, namely from the gas inlet 6 on the right to the gas outlet 7 on the left.

To this end, the oxygen is fed continuously through the gas inlet on the right, and the pressure acting in the hollow fiber 5 is controlled by a pressure controller 8, which is disposed in the region of the gas outlet and can be configured, for example, such that the effective cross-section of the hollow fiber 5 can be reduced or expanded.

If the cross-section here is reduced by the pressure controller 8, the pressure in the hollow fiber 5 increases, such that it inflates and takes up a larger volume, whereby in the region 5', which is defined by the surface of the inflated hollow fiber 5, blood is displaced from the chamber 2. In order to implement a defined flow direction, namely from blood inlet 3 to blood outlet 4, an inlet valve 9 is installed at the blood inlet 3 and an outlet valve 10 is installed at the blood outlet 4, with both valves operating as one-way valves in the same direction.

In this way, it is ensured that upon a displacement, i.e., an inflation of the elastically deformable hollow fiber 5, blood is pushed out of the chamber 2 only through the blood outlet 4, and upon a reduction of the volume of the fiber 5, the resulting negative pressure and the closed outlet valve 10 cause new blood to be treated to be suctioned into the chamber 2 through the blood inlet 3 and the inlet valve 9.

In this embodiment according to FIG. 2, it is apparent that the elastically deformable fiber 5 not only implements the pump function inside the device 1, but due to the fact that this fiber at the same time is mass and/or energy-permeable, the mass transfer, i.e., the gas exchange in this example, can also take place between the blood and the gas phase.

Figure 3:
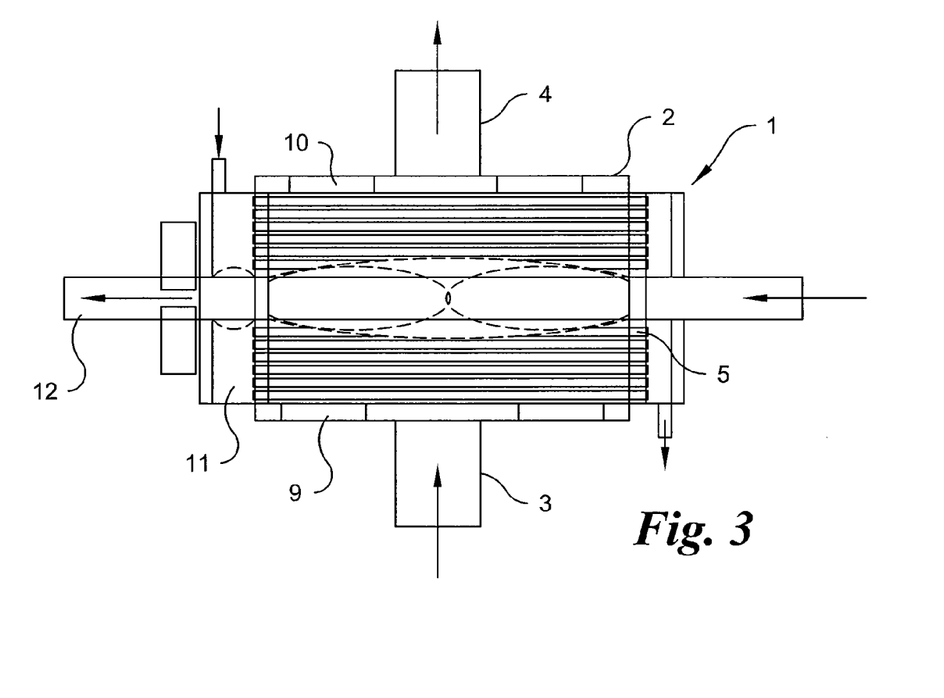
FIG. 3 is a schematic view of a two-chamber model of a blood oxygenator according to another embodiment of the present invention.

In contrast, FIG. 3 shows another preferred embodiment of a blood oxygenator as a total device 1, in which both the above-mentioned chamber 2 and also another chamber 11 are disposed. The design here is substantially comparable to that from FIG. 2. However, a central elastically deformable hollow fiber 12, which is used to implement the pump function but is not used for the mass transfer, extends through the chamber 2 and the chamber 11.

To this end, the chamber 11 serves for the supply of the second medium in the spirit of the invention, that is for an application as a blood oxygenator for the supply of oxygen, which then is distributed to a plurality of mass-permeable hollow fibers 5, which extend substantially transversely to the blood flow through the chamber 2.

Here too, blood is pumped through a blood inlet 3 into the chamber 2 and out of the chamber 2 through the blood outlet 4, wherein again valves 9, 10 are used to define the flow direction. The key difference compared to FIG. 2 here, in addition to the high number of mass-permeable hollow fibers 5, which are disposed around the central, elastically deformable hollow fiber 12, is the additional characteristic according to the invention that the hollow fiber 12 has an elastically deformable region also in the chamber 11, so that upon a pressure increase inside the hollow fiber 12, blood is displaced not only in the chamber 2, but a pressure increase also takes place in the chamber 11, which continues to the individual mass-permeable hollow fibers 5.

In addition to the pump effect in the chamber 2, due to periodic pressure fluctuations in the hollow fiber 12, a periodic pressure fluctuation in the chamber 11 is also obtained, and on the inside of the mass-permeable hollow fibers 5, such that in addition the gas boundary layer on the inside of the hollow fibers 5 is disturbed.

Figure 4:
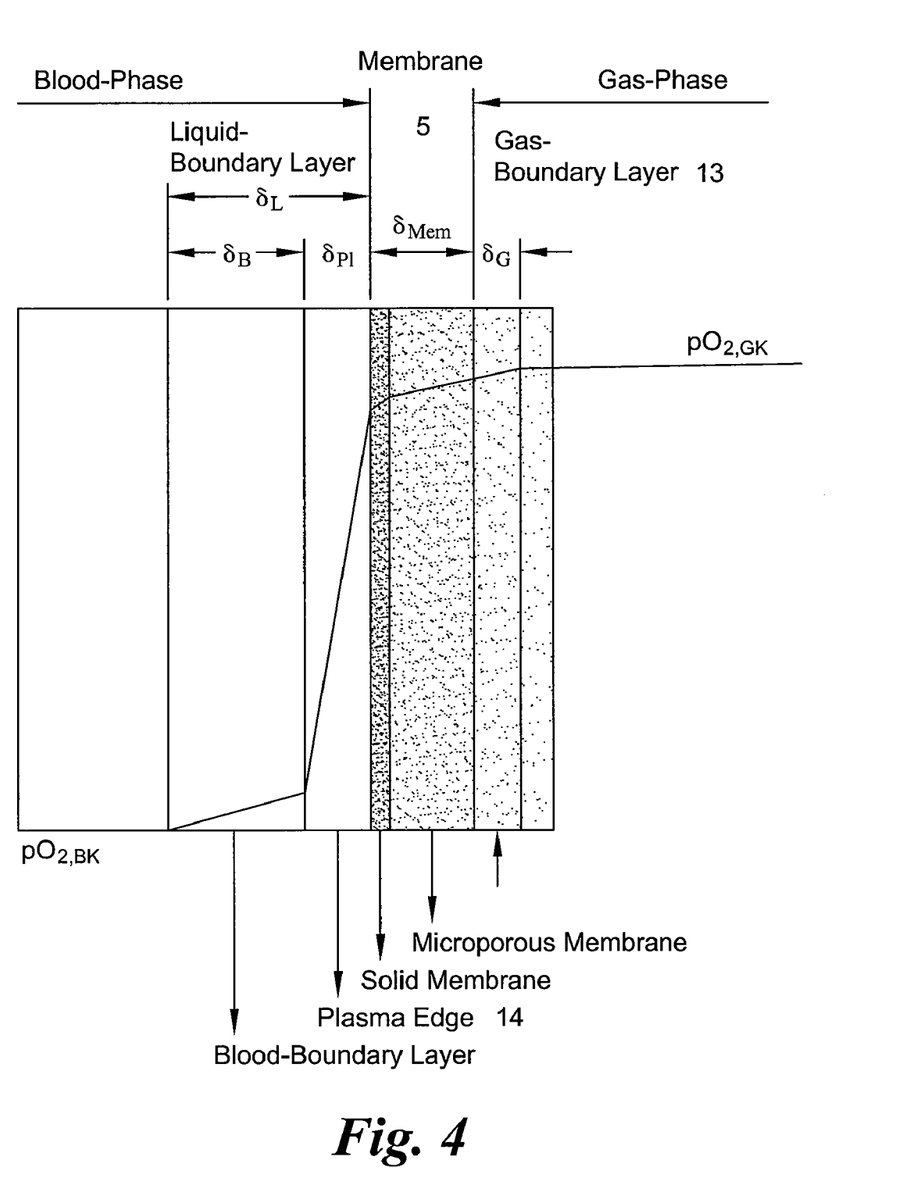
FIG. 4 is a schematic diagram basically illustrating the oxygen exchange in a blood oxygenator on the boundary layer of a microporous membrane.

The relationships present during a mass transfer in a blood oxygenator of the above-described kind are illustrated in more detail in FIG. 4, for example. In FIG. 4 a membrane 5 is apparent, which can be provided, for example, by the wall of a mass-permeable hollow fiber 5 of the above-mentioned exemplary embodiment. From inside the hollow fiber, the gas phase acts due to an increased oxygen partial pressure $pO_2$. Directly abutting the membrane 5 is a gas boundary layer 13, in which the gas exchange takes place, so that the $CO_2$ taken up from the blood is enriched at this boundary layer. Due to this enrichment, the effectiveness of the gas exchange, i.e., the transfer of oxygen into the blood, is reduced.

The embodiment according to FIG. 3, with the pulsation generated in the chamber 11, brings about a destruction of this gas boundary layer 13, so that oxygen can reach the boundary regions of the membrane 5 more easily, thereby increasing the effectiveness of the overall gas exchange.

Similarly, the pump function generated internally in the chamber 2 causes periodic pressure fluctuations inside the chamber 2, by which a plasma edge 14 formed on the blood side on the membrane 5 with blood oxygenators is disturbed. Due to this disturbance of the plasma edge 14, the effectiveness of the mass transfer can likewise be increased. The diagram of the oxygen partial pressure shows that the primarily relevant oxygen transfer takes place inside the plasma edge, i.e., here the oxygen partial pressure drops off significantly from the gas phase on the right to the blood phase on the left. Precisely the disturbance of the plasma edge by the pressure fluctuations occurring in the chamber 2, which are generated by the deformation of the elastic membrane, can therefore contribute significantly to increasing the efficiency of the transfer rates.

Figure 5:
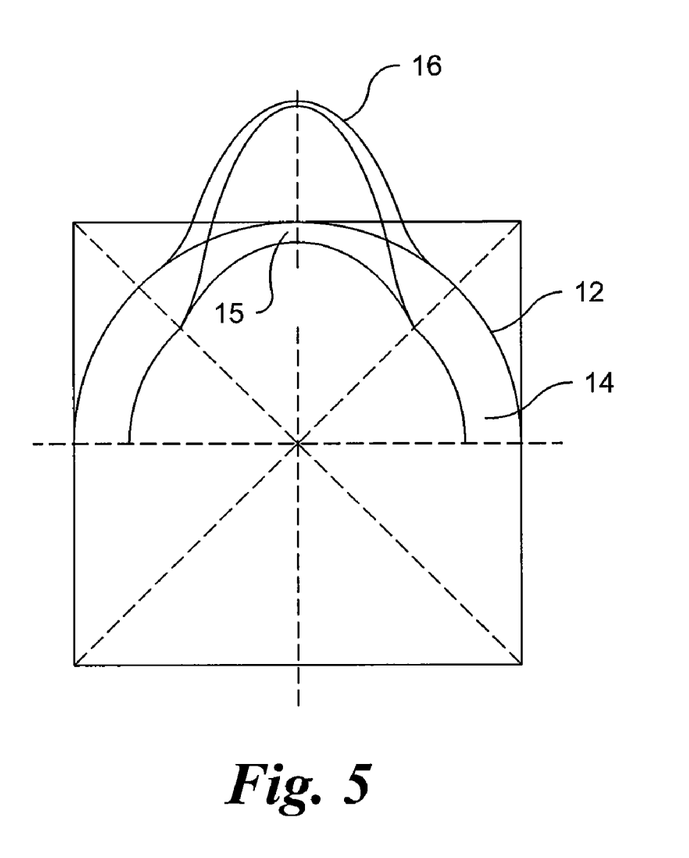
FIG. 5 is a transverse, schematic view of an elastically deformable hollow fiber having a partially reduced wall thickness according to an embodiment of the present invention.

FIG. 5 furthermore shows a possible embodiment of an elastically deformable hollow fiber 12. The elastically deformable fiber 12 shown here has a thick wall region 14 and in part also a wall region 15, whose thickness is reduced, so that in the case of a pressure increase on the inside of this hollow fiber 12 a bulging 16 will develop substantially where the thickness reduction 15 is provided. This is where the hollow fiber 12 has been weakened the most, so that this wall region 15 will give way fastest under the pressure increase. With this embodiment it is thus possible to achieve a deformation of an elastic hollow fiber 12 in only one desired region through the arrangement of defined wall reductions, whereby, for example, also the maximum achievable volume change of the hollow fiber 12 can be defined.

Figure 6A:
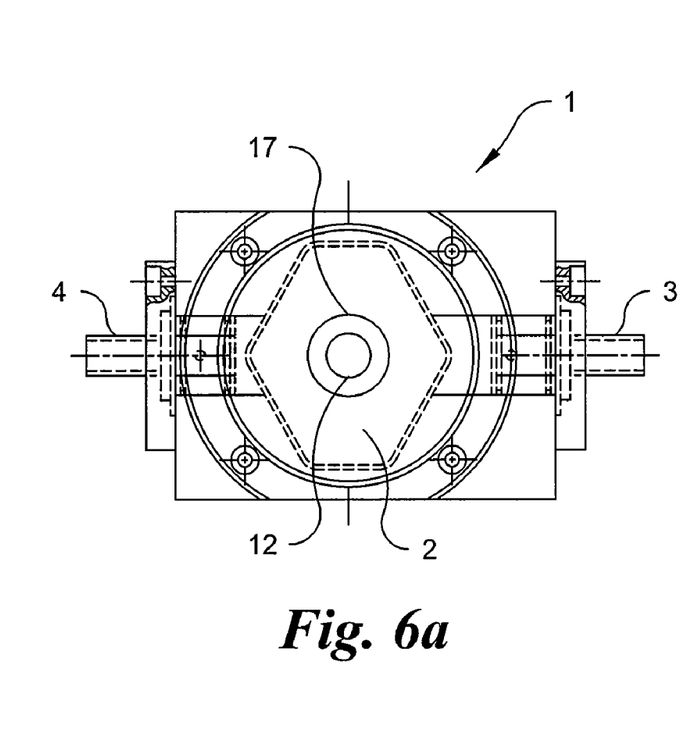
FIGS. 6 and 6b are schematic views of a potential housing shape according to embodiments of the present invention.
Figure 6B:
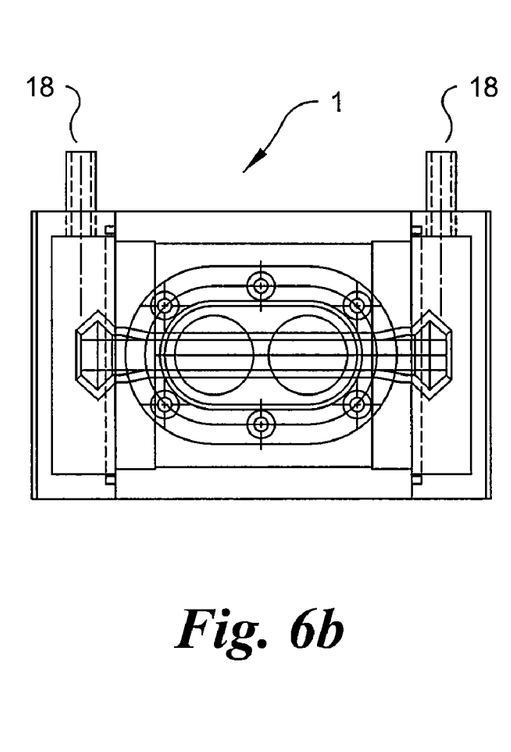

FIGS. 6a and 6b show an example of the housing of a device according to the invention. In FIG. 6a, a cross-sectional view of the chamber 2 through which the blood flows is apparent, having a substantially hexagonal cross-section. The rigid mass-permeable hollow fibers, which are not shown, are disposed perpendicular to the sheet plane and thus extend transversely to the flow direction of the blood, which flows from the blood inlet 3 to the blood outlet 4.

Centrally on the inside of the chamber, a cylindrical region 17 of permeable hollow fibers has been spared, and a deformable elastic hollow fiber 12 is disposed centrally therein in order to implement the pump function. In FIG. 6b, the connections 18 are shown for pressurizing the hollow fibers with a medium. The oxygen connections are not shown here.

Overall, when looking at the invention, it is apparent that compact oxygenators can be implemented, which can be provided both for use in babies, particularly premature babies, and as implantable organs.

With respect to all embodiments, it should be noted here that the technical features mentioned in connection with an embodiment can be used not only with that specific embodiment, but also with the respective other embodiments, which are mentioned or also not mentioned within the scope of this description. All technical features disclosed in this description of the invention shall be considered key elements of the invention and can be arbitrarily combined with each other, or used alone.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for mass transfer and/or energy exchange between a first medium and a second medium, optionally between blood and a gas/gas mixture, the device comprising a first chamber through which the first medium flows, at least one mass-permeable and/or energy-permeable hollow fiber arranged in the first chamber, such that the second medium flows through the permeable hollow fiber and the first medium flows around the permeable hollow fiber, at least one pump element arranged within the first chamber as an elastically deformable hollow fiber which displaces the first medium from the first chamber and/or sucks the first medium into the first chamber by pumping, wherein the at least one mass-permeable and/or energy-permeable hollow fiber is only used for the mass transfer and/or energy exchange.

2. The device according to claim 1, wherein the at least one elastically deformable hollow fiber is configured to be acted upon by the second medium.

3. The device according to claim 1, wherein the at least one elastically deformable hollow fiber is configured not to be acted upon by the second medium but by a third fluid medium.

4. The device according to claim 1, wherein the at least one mass-permeable and/or energy-permeable hollow fiber is configured as a rigid hollow fiber.

5. The device according to claim 1, wherein a one-way valve is arranged in the first chamber at each of an inlet and an outlet of the first chamber to define a flow direction of the first medium.

6. The device according to claim 1, wherein the at least one elastically deformable hollow fiber is configured as a mass-permeable and/or energy-permeable hollow fiber.

7. The device according to claim 1, comprising a plurality of mass-permeable and/or energy-permeable hollow fibers, wherein at least some of the mass-permeable and/or energy-permeable hollow fibers are configured as elastically deformable hollow fibers.

8. The device according to claim 1, wherein at least one of the at least one elastically deformable hollow fiber and the at least one mass-permeable and/or energy-permeable hollow fiber is configured as a silicone hose.

9. The device according to claim 1, wherein a medium for acting upon the at least one elastically deformable hollow fiber comprises a fluid which exchanges energy, optionally heat energy, with the first medium.

10. The device according to claim 1, further comprising at least one additional chamber which supplies the second medium to the at least one mass-permeable and/or energy-permeable hollow fiber, wherein the at least one elastically deformable hollow fiber extends through the first chamber and the at least one additional chamber.

11. The device according to claim 10, wherein a surface/volume of the at least one elastically deformable hollow fiber is changeable at least in some areas in the at least one additional chamber by being internally acted upon by the second medium, such that with a surface/volume change pressure variations can be generated in the second medium.

12. The device according to claim 1, wherein surface/volume changes of the at least one elastically deformable hollow fiber can be generated by pressure changes in the second medium flowing through at least on elastically deformable hollow fiber.

13. The device according to claim 12, wherein the pressure changes can be generated by a continuous inflow of the second medium into the at least one elastically deformable hollow fiber at an entrance to the device and a quantitatively controllable outflow at an exit of the device, optionally by a cross-section which can be varied in a controlled manner.

14. The device according to claim 1, further comprising at least one supporting element surrounding the at least one elastically deformable hollow fiber, wherein the supporting element comprises at least one ring or tube or lattice for generating at least one locally confined area of a surface/volume change.

15. The device according to claim 14, wherein the at least one elastically deformable hollow fiber has a variable wall thickness and/or surface profiling in some sections for generating at least one locally confined area of a surface/volume change.

16. The device according to claim 1, wherein the at least one elastically deformable hollow fiber is symmetrically surrounded by a plurality of non-elastic and not mass-permeable and/or energy-permeable hollow fibers.

17. The device according to claim 16, wherein an overall arrangement of hollow fibers has an essentially polygonal, optionally hexagonal, cross-section.

18. The device according to claim 16, wherein the non-elastic and not mass-permeable and/or energy-permeable hollow fibers are layered offset from each other, optionally by half a distance between two hollow fibers.

19. The device according to claim 1, wherein the first chamber has a filling volume of the first medium which is less than a blood volume of a baby, optionally less than 100 ml.

20. The device according to claim 1, which is adapted for use as a blood oxygenator for premature or newborn babies, infants and adults, optionally as an implantable oxygenator.

21. The device according to claim 1, which is adapted for use as an implantable artificial organ, optionally as a dialysis machine.

* * * * *